United States Patent
Kaneumi et al.

(10) Patent No.: US 8,361,215 B2
(45) Date of Patent: Jan. 29, 2013

(54) POLYFLUOROALKYLPHOSPHONIC ACID SALT EMULSIFIER AND MOLD-RELEASING AGENT COMPRISING THE SAME AS ACTIVE INGREDIENT

(75) Inventors: Yoshiyama Kaneumi, Ibaraki (JP); Seiichiro Murata, Ibaraki (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 13/508,124

(22) PCT Filed: Oct. 7, 2010

(86) PCT No.: PCT/JP2010/067616
§ 371 (c)(1),
(2), (4) Date: May 4, 2012

(87) PCT Pub. No.: WO2011/055609
PCT Pub. Date: May 12, 2011

(65) Prior Publication Data
US 2012/0214148 A1    Aug. 23, 2012

(30) Foreign Application Priority Data

Nov. 4, 2009 (JP) .................. 2009-252620
Nov. 24, 2009 (JP) .................. 2009-266189

(51) Int. Cl.
*B01F 17/14* (2006.01)
*B29C 33/60* (2006.01)
*B29C 33/56* (2006.01)
*B28B 7/38* (2006.01)
*C07F 9/38* (2006.01)
*C09K 3/00* (2006.01)

(52) U.S. Cl. ......... 106/38.22; 106/2; 106/38.2; 435/1.1; 516/56; 562/25; 570/134

(58) Field of Classification Search ............. 106/2, 38.2, 106/38.22; 435/1.1; 516/56; 562/25; 570/134
See application file for complete search history.

(56) References Cited

U.S. PATENT DOCUMENTS

| | | | |
|---|---|---|---|
| 8,197,586 B2 * | 6/2012 | Kaneumi et al. | 106/38.22 |
| 2012/0077930 A1 * | 3/2012 | Kaneumi et al. | 524/612 |
| 2012/0108849 A1 * | 5/2012 | Murata et al. | 568/14 |
| 2012/0174822 A1 * | 7/2012 | Kaneumi et al. | 106/38.22 |
| 2012/0180696 A1 * | 7/2012 | Kaneumi et al. | 106/38.22 |

FOREIGN PATENT DOCUMENTS

| | | |
|---|---|---|
| JP | 52-036588 | 3/1977 |
| JP | 52-039587 | 3/1977 |
| JP | 55-133490 | 10/1980 |
| JP | 58-180597 | 10/1983 |
| JP | 59-166596 | 9/1984 |
| JP | 60-190309 | 9/1985 |
| JP | 60-193615 | 10/1985 |
| JP | 2000-072601 | 3/2000 |
| JP | 4506894 B1 * | 7/2010 |
| JP | 2010-189289 A * | 9/2010 |
| WO | WO 03/102003 A1 | 12/2003 |
| WO | WO 2007/105633 A1 | 9/2007 |
| WO | WO 2010/104065 A1 | 9/2010 |
| WO | WO2011/148795 A1 * | 12/2011 |

OTHER PUBLICATIONS

International Preliminary Report on Patentability and Written Opinion from corresponding PCT application No. PCT/JP2010/067616 dated Jun. 21, 2012 (6 pgs).
International Search Report from corresponding related PCT application No. PCT/JP2010/067616 dated Jan. 11, 2011 (4 pgs).

\* cited by examiner

*Primary Examiner* — Anthony J Green
(74) *Attorney, Agent, or Firm* — Brinks Hofer Gilson & Lione

(57) ABSTRACT

Disclosed is an emulsifier comprising, as an active ingredient, a polyfluoroalkylphosphonic acid salt represented by the general formula: $C_nF_{2n+1}(CH_2CF_2)_a(CF_2CF_2)_b(CH_2CH_2)_cP(O)(OM^1)(OM^2)$, wherein $M^1$ is a hydrogen atom, an alkali metal, an ammonium base, or an organic amine base, $M^2$ is an alkali metal, an ammonium base, or an organic amine base, n is an integer of 1 to 6, a is an integer of 1 to 4, b is an integer of 1 to 3, and c is an integer of 1 to 3. An aqueous solution or organic solvent solution of the emulsifier can be effectively used to emulsify a perfluoropolyether oil or a perfluorocarbon compound. The resulting emulsion exhibits excellent emulsification stability, and thus can be effectively used as a mold-releasing agent.

16 Claims, No Drawings

POLYFLUOROALKYLPHOSPHONIC ACID SALT EMULSIFIER AND MOLD-RELEASING AGENT COMPRISING THE SAME AS ACTIVE INGREDIENT

RELATED APPLICATION

This application is a 35 U.S.C. §371 national phase filing of International Patent Application No. PCT/JP2010/067616, filed Oct. 7, 2010, through which and to which priority is claimed under 35 U.S.C. §119 to Japanese Patent Application Nos. 2009-252620, filed Nov. 4, 2009 and 2009-266189, filed Nov. 24, 2009.

TECHNICAL FIELD

The present invention relates to a polyfluoroalkylphosphonic acid salt emulsifier and a mold-releasing agent comprising the same as an active ingredient. More particularly, the present invention relates to a polyfluoroalkylphosphonic acid salt emulsifier that can be effectively used, for example, as an emulsifier in the formation of an emulsion of a perfluoropolyether oil or perfluorocarbon compound; and a mold-releasing agent comprising the same as an active ingredient.

BACKGROUND ART

Currently, silicone oil, wax, talc, mica, tetrafluoroethylene resin, and other mold-releasing agents are used in the molding of polymeric materials, such as plastic materials and rubber materials, using molds. Although silicone oil, wax, etc., have excellent mold releasability, such mold-releasing agents are transferred to molded products, thereby impairing uniform coating properties, secondary processability, and other properties; in addition, durability is not sufficient. As for tetrafluoroethylene resin, the durability of mold release effect and secondary processability are satisfactory; however, it is necessary to perform bake treatment to form a film on the molding surface of a mold in the mold-release process, and the same treatment is required for reprocessing. Consequently, many processes are required.

In order to solve these defects, mold-releasing agents comprising a $C_4$-$C_{20}$ polyfluoroalkyl group-containing phosphate ester as one of their active ingredients are proposed (see Patent Documents 1 to 3). These mold-releasing agents exhibit excellent mold releasability and have a longer mold release life than conventional mold-releasing agents; however, due to the recent trend toward the more complicated shape of molded products, there is a demand for mold-releasing agents having much higher performance.

Meanwhile, polyfluoroalkyl phosphonates are also widely used as starting materials for the synthesis of mold-releasing agents. Compounds having a $C_8$-$C_{12}$ perfluoroalkyl group are most likely to develop mold release performance when used as mold-releasing agents. In particular, phosphonate compounds having a perfluorooctyl group and represented by the general formula:

$$CF_3(CF_2)_7CH_2CH_2P(O)(OC_2H_5)_2$$

are preferably used for this kind of application (see Patent Documents 4 to 7).

Incidentally, it is reported that telomer compounds having a $C_8$-$C_{12}$ perfluoroalkyl group are biologically degraded in the environment and converted to compounds having relatively high bioaccumulation and environmental concentration, causing concerns for exposure during treatment processes, and for release or diffusion from waste, treated substrates, etc., into the environment. Moreover, compounds having a perfluoroalkyl group containing 14 or more carbon atoms are very difficult to handle because of their physical and chemical properties, and hence, such compounds are rarely used in practice.

Furthermore, as for telomer compounds having a perfluoroalkyl group containing 8 or more carbon atoms, generation and mixing of perfluorooctanoic acids with high bioaccumulation potential is unavoidable during the production of these compounds. For these reasons, companies that produce such telomer compounds have retreated from the production of the compounds or promoted the use of alternative compounds having a perfluoroalkyl group containing 6 or less carbon atoms.

However, compounds having a perfluoroalkyl group containing 6 or less carbon atoms cause a significant decrease in orientation on the surface of a treated substrate, and the melting point, glass transition point (Tg), etc., of the compounds are markedly lower than those of $C_8$ compounds. Accordingly, the compounds are highly influenced by their environmental conditions, such as temperature, humidity, stress, and contact with organic solvents. Consequently, the desired performance cannot be sufficiently achieved, and durability and other properties are affected.

Moreover, perfluoropolyether oil widely used as a lubricant is often used in the form of an emulsion for medicinal and cosmetic uses. The emulsifier usable in this case is a $C_8$-$C_{12}$ polyfluoroalkylcarboxylic acid, preferably a pentadecafluorooctanoic acid ammonium salt, which are generally used in emulsion polymerization or suspension polymerization.

Pentadecafluorooctanoic acid ammonium $C_7F_{15}COONH_4$ is particularly excellent in emulsification performance and cost; however, due to environmental concerns, there is a tendency to inhibit the use of pentadecafluorooctanoic acid ammonium in terms of the number of carbon atoms of the perfluoroalkyl group.

PRIOR ART DOCUMENT

Patent Document

Patent Document 1: JP-B-53-23270
Patent Document 2: JP-B-53-23271
Patent Document 3: JP-B-57-48035
Patent Document 4: JP-B-2-45572
Patent Document 5: JP-B-3-78244
Patent Document 6: JP-B-4-4923
Patent Document 7: JP-B-4-11366
Patent Document 8: WO 2007/105633 A1
Patent Document 9: JP-A-2000-72601

OUTLINE OF THE INVENTION

Problem to be Solved by the Invention

An object of the present invention is to provide an emulsifier that is a compound having a perfluoroalkyl group containing 6 or less carbon atoms, which is said to have low bioaccumulation potential, and having emulsification performance equivalent to the excellent emulsification performance of pentadecafluorooctanoic acid ammonium; and to provide a mold-releasing agent comprising the same as an active ingredient.

Means for Solving the Problem

The above object of the present invention can be accomplished by an emulsifier comprising, as an active ingredient, a polyfluoroalkylphosphonic acid salt represented by the general formula:

$$C_nF_{2n+1}(CH_2CF_2)_a(CF_2CF_2)_b(CH_2CH_2)_cP(O)(OM^1)(OM^2) \quad \text{(I)}$$

wherein M' is a hydrogen atom, an alkali metal, an ammonium base, or an organic amine base, $M^2$ is an alkali metal, an ammonium base, or an organic amine base, n is an integer of 1 to 6, a is an integer of 1 to 4, b is an integer of 1 to 3, and c is an integer of 1 to 3; and by a mold-releasing agent comprising the same as an active ingredient.

An aqueous solution or organic solvent solution of the emulsifier can be effectively used to emulsify a perfluoropolyether oil or a perfluorocarbon compound.

Effect of the Invention

The polyfluoroalkylphosphonic acid salt emulsifier, particularly ammonium salt emulsifier, according to the present invention is a compound having a perfluoroalkyl group containing 6 or less carbon atoms, which is said to have low bioaccumulation potential, and having emulsification performance equivalent to the excellent emulsification performance of pentadecafluorooctanoic acid ammonium. An emulsion formed using an aqueous solution or organic solvent solution of the emulsifier, and a perfluoropolyether oil or a perfluorocarbon compound is stable. The emulsification stability of the emulsion is maintained at an excellent level even after being left for one month at room temperature or 40° C.

The emulsion with a perfluoropolyether oil can be suitably used for surface-treating agents, particularly for mold-releasing agents, cosmetic materials, etc., while maintaining excellent emulsification stability. Moreover, perfluorocarbon compounds can dissolve and carry a large amount of oxygen; therefore, the emulsion of a perfluorocarbon compound emulsified with the emulsifier can be effectively used as an oxygen transport medium or organ storage solution.

Particularly for use in mold-releasing agents, for example, when the emulsion is prepared as an aqueous or organic solvent mold-releasing agent having a concentration of about 0.1 wt. % or less, the mold-releasing agent exhibits effective mold releasability when applied to an object to be subjected to mold release (e.g., a molding mold). This excellent effect is attributable to the extremely high solubility of the polyfluoroalkylphosphonic acid salt in solvents. A mold-releasing agent, whose mold releasability is much more excellent than conventional mold-releasing agents prepared to have a solid matters content of 0.5 wt. %, can be obtained with a solid matters content of about 0.1 wt. % or less.

Moreover, the excellent solubility of the polyfluoroalkylphosphonic acid salt in solvents facilitates, when diluted with a diluent, the formation of mold-releasing agent solutions with uniform concentration. Accordingly, precipitation problematically formed in conventional mold-releasing agents is not formed, and good storage stability is ensured.

Owing to the above-described various properties of the polyfluoroalkylphosphonic acid salt, the mold-releasing agent, preferably emulsion-type mold-releasing agent, according to the present invention exhibits the following excellent effects:

(1) Film-forming properties are excellent, allowing the formation of uniform coating on molded products of a complicated shape.

(2) Film-forming properties for the mold surface and adhesion to the mold surface due to ionic groups are excellent, significantly improving mold releasability and mold release life.

(3) Mold releasability and sustainability are excellent even after dilution to low concentration (e.g., about 0.1 wt. %), reducing mold contamination caused by the mold-releasing agent.

(4) Since the transmission of the mold-releasing agent to the molded product is low, the quality of the molded product after molding is less adversely affected, improving the dimensional accuracy of the molded product.

EMBODIMENTS FOR CARRYING OUT THE INVENTION

A polyfluoroalkylphosphonic acid used as an emulsifier in the form of a salt is represented by the general formula:

$$C_nF_{2n+1}(CH_2CF_2)_n(CF_2CF_2)_b(CH_2CH_2)_cP(O)(OH)_2 \quad (II)$$

wherein n is an integer of 1 to 6, a is an integer of 1 to 4, b is an integer of 1 to 3, and c is an integer of 1 to 3. This compound is produced by the hydrolysis of a polyfluoroalkylphosphonic acid diester represented by the general formula:

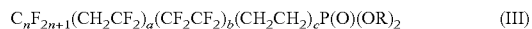

$$C_nF_{2n+1}(CH_2CF_2)_a(CF_2CF_2)_b(CH_2CH_2)_cP(O)(OR)_2 \quad (III)$$

wherein R is an alkyl group having 1 to 4 carbon atoms.

The polyfluoroalkylphosphonic acid diester [III], which is used as a starting material for this reaction, is obtained by the reaction of a polyfluoroalkyl iodide of the formula:

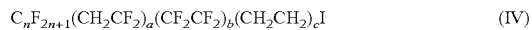

$$C_nF_{2n+1}(CH_2CF_2)_a(CF_2CF_2)_b(CH_2CH_2)_cI \quad (IV)$$

with trialkyl phosphite $P(OR)_3$. The polyfluoroalkyl iodide [IV] is a known compound and is disclosed in Patent Document 8.

The polyfluoroalkyl iodide [IV] can be reacted with trialkyl phosphite $P(OR)_3$ having an alkyl group containing 1 to 4 carbon atoms, such as trimethyl phosphite, triethyl phosphite, tripropyl phosphite, or tributyl phosphite, to perform the RI-elimination reaction, thereby obtaining the polyfluoroalkylphosphonic acid diester [III], which is used as a starting material.

The hydrolysis reaction of the polyfluoroalkylphosphonic acid diester [III] can be readily carried out by stirring at about 90 to 100° C. in the presence of an acidic catalyst, such as inorganic acid typified by concentrated hydrochloric acid. The resulting reaction mixture is filtered under reduced pressure, followed by water washing/filtration, acetone washing/filtration, and other methods, thereby obtaining the target polyfluoroalkylphosphonic acid [II] with a good yield of 90% or more.

The polyfluoroalkylphosphonic acid salt of the formula:

$$C_nF_{2+1}(CH_2CF_2)_a(CF_2CF_2)_b(CH_2CH_2)_cP(O)(OM^1)(OM^2) \quad (I)$$

which is used as an emulsifier, is obtained by reacting a polyfluoroalkylphosphonic acid of the formula:

$$C_nF_{2n+1}(CH_2CF_2)_n(CF_2CF_2)_b(CH_2CH_2)_cP(O)(OH)_2 \quad (II)$$

with an aqueous alkali metal hydroxide solution, an aqueous ammonia solution, or an organic amine.

Preferred examples of the alkali metal hydroxide include sodium hydroxide, potassium hydroxide, and the like. Preferred examples of the organic amine include mono ethylamine, monoisopropylamine, diethylamine, diisopropanolamine, dicyclohexylamine, triethylamine, monoethanolamine, diethanolamine, triethanolamine, tris(2-hydroxyethyl)amine, pyridine, morpholine and derivatives thereof. The alkali metal hydroxide, ammonia, or organic amine forms mono-salts when used in an amount equimolar to the polyfluoroalkylphosphonic acid, and forms di-salts when used in an amount of two times the mole of the polyfluoroalkylphosphonic acid. Generally, the alkali metal hydroxide, ammonia, or organic amine is used in an amount not less than the theoretically required number of moles. When the alkali metal hydroxide, ammonia, or organic amine is used in an amount equimolar or more to less than two times the mole of the polyfluoroalkylphosphonic acid, a mixture of mono-salts and di-salts is formed.

The polyfluoroalkylphosphonic acid salt is used as an aqueous solution in which the salt is dissolved in an aqueous medium (water or a water-soluble organic solvent aqueous solution), or as an organic solvent solution in which the salt is dissolved in an organic solvent. Examples of the organic solvent include alcohols, such as methanol, ethanol, and isopropanol; ketones, such as acetone, methyl ethyl ketone, and methyl isobutyl ketone; and aprotic polar solvents, such as acetonitrile, dimethylformamide, diethylformamide, dimethylacetamide, and N-methyl-2-pyrrolidone.

As for the emulsification ability of the polyfluoroalkylphosphonic acid salt, in the case of, for example, a 2-(perfluorohexyl)ethyl phosphonic acid ammonium aqueous solution, the critical micelle concentration [CMC] of the solution appears at an emulsifier concentration of about 0.8 wt. %, and the solution has constant low surface tension at an emulsifier concentration of about 1.0 wt. % or more.

The aqueous solution or organic solvent solution of the emulsifier is added to the perfluoropolyether oil so that the active ingredient amount thereof is about 0.01 to 30 parts by weight, preferably about 0.1 to 15 parts by weight, based on 100 parts by weight of perfluoropolyether oil. The mixture is then subjected to an emulsification treatment to form a perfluoropolyether oil emulsion. When the emulsifier is used in an amount greater than this range, the perfluoropolyether oil cannot sufficiently exhibit its characteristics. The emulsification treatment is performed in such a manner that preliminary emulsification is carried out using a homogenizer, etc., at a rotational speed of about 500 to 10,000 rpm, and emulsification is further carried out using a high-pressure homogenizer at a pressure of about 100 to 800 kgf/cm$^2$ (about 10 to 80 MPa).

As the perfluoropolyether oil to be emulsified, one represented by the general formula:

$$RfO(C_3F_6O)_p(C_2F_4O)_q(CF_2O)_rRf' \tag{XI}$$

is used. In this formula, Rf and Rf' are perfluoro-lower alkyl groups having 1 to 5 carbon atoms (e.g., perfluoromethyl groups and perfluoroethyl groups), $C_3F_6O$, $C_2F_4O$, and $CF_2O$ groups are bonded randomly, p+q+r is 2 to 200, and p, q, or r may be 0. Specific examples of the perfluoropolyether oil represented by the above general formula are as follows.

$$RfO[CF(CF_3)CF_2O]mRf' \tag{XIa}$$

In this formula, m is 2 to 200. This perfluoropolyether oil is obtained by complete fluorination of a precursor produced by photooxidation polymerization of hexafluoropropene. Alternatively, this oil is obtained by anionic polymerization of hexafluoropropene oxide in the presence of a cesium fluoride catalyst, and fluorine-gas treatment of the obtained acid fluoride compound having a terminal —CF(CF$_3$)COF group.

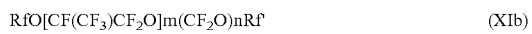

$$RfO[CF(CF_3)CF_2O]m(CF_2O)nRf' \tag{XIb}$$

In this formula, CF(CF$_3$)CF$_2$O and CF$_2$O groups are bonded randomly, m+n is 3 to 200, and m:n is (10:90) to (90:10). This perfluoropolyether oil is obtained by complete fluorination of a precursor produced by photooxidation polymerization of hexafluoropropene.

$$RfO(CF_2CF_2O)m(CF_2O)nRf' \tag{XIc}$$

In this formula, m+n is 3 to 200, and m:n is (10:90) to (90:10). This perfluoropolyether oil is obtained by complete fluorination of a precursor produced by photooxidation polymerization of tetrafluoroethylene.

Perfluoropolyether oils other than those represented by the above general formulae can also be used. For example, the following perfluoropolyether oil can be used.

$$F(CF_2CF_2CF_2O)nCF_2CF_3 \tag{XII}$$

In this formula, n is 2 to 100. This perfluoropolyether oil is obtained by anionic polymerization of 2,2,3,3-tetrafluorooxetane in the presence of a cesium fluoride catalyst, and fluorine-gas treatment of the obtained fluorine-containing polyether (CH$_2$CF$_2$CF$_2$O)n under ultraviolet irradiation at 160 to 300° C.

These perfluoropolyether oils listed as specific examples can be used singly or in combination; however, in terms of cost performance, the perfluoropolyether oil [XIa] or [XIb], particularly the perfluoropolyether oil [XIa], is preferably used. A usable example of the perfluoropolyether oil [XIa] is one in which m is an integer of 2 to 100, and the number average molecular weight (Mn) is about 300 to 50,000, preferably about 500 to 20,000.

The kinetic viscosity of these perfluoropolyether oils is not limited; however, those having a kinetic viscosity of 5 to 2,000 mm$^2$/s (40° C.) are used as lubricants. In terms of use under high temperature conditions, those having a kinetic viscosity of 100 to 1,500 mm$^2$/s (40° C.) are preferably used. More specifically, perfluoropolyether oils having a kinetic viscosity of about 5 mm$^2$/s or less are largely evaporated, and do not comply with the requirements for the standard of JIS ball-and-roller bearing grease, class 3 specified as heat-resistant grease (i.e., the amount of evaporation is 1.5% or less). Conversely, perfluoropolyether oils having a kinetic viscosity of 2,000 mm$^2$/s or more have a pour point (according to JIS K2283 corresponding to ISO 2909 and ISO 3104) of 10° C. or more; bearings cannot be rotated by an ordinary method at the time of low-temperature starting; and they must be heated to make them usable.

Moreover, the perfluoropolyether oil emulsion is used as an aqueous solution or organic solvent solution in which the emulsion is further diluted with an aqueous solution or organic solvent so as to have a solid matters content of about 0.01 to 30 wt. %, preferably about 0.05 to 10 wt. %, thereby forming a surface-treating agent, such as water- and oil-repellent agent, anti-adhesion agent, or mold-releasing agent, while maintaining excellent emulsification stability. When the emulsion is used as a mold-releasing agent, the agent is applied to the surface of a molding mold. When applied on a substrate, such as a molded product, the emulsion is used as an anti-adhesion agent.

When used as a mold-releasing agent, the emulsion is diluted with water or an organic solvent. The organic solvent used is at least one of alcohols, such as methanol, ethanol, n-propanol, and isopropanol; ketones, such as acetone, methyl ethyl ketone, and methyl isobutyl ketone; ethers, such as diethyl ether, diisopropyl ether, dioxane, and tetrahydrofuran; esters, such as ethyl acetate and butyl acetate; polyhydric alcohol derivatives, such as methyl cellosolve, ethyl cellosolve, methyl carbitol, and ethyl carbitol; halogenated hydrocarbons, such as carbon tetrachloride, methylene chloride, trichloroethylene, perchloroethylene, trichloroethane, trichlorofluoromethane, tetrachlorodifluoroethane, and trichlorotrifluoroethane; and the like. Preferably, a mixed solvent of isopropanol and ethanol is used. Here, the organic solvent can be used in combination with water.

The mold-releasing agent solution can be applied to a mold by any common method, such as dipping, spraying, brushing, aerosol spraying, or impregnated fabric coating. Moreover, examples of molding materials to be molded with a mold to which the mold-releasing agent is applied include polyurethane, polycarbonate, epoxy resin, phenol resin, polyimide resin, vinyl chloride resin, and other resins; natural rubber, chloroprene rubber, fluororubber, and other rubbers.

In addition, the perfluorocarbon compound capable of dissolving and carrying a large amount of oxygen can be effectively used as an oxygen transport medium or a storage solution for isolated organs in the form of an emulsion containing the polyfluoroalkylphosphonic acid salt (see Patent Document 9).

Examples of the perfluorocarbon compound include perfluorocyclohexane, perfluorodecalin, perfluorotrimethylcyclohexane, perfluoroisopropylcyclohexane, perfluoromethyldecalin and other perfluorocycloalkanes, or their perfluoroalkyl derivatives. The emulsion of the perfluorocarbon compound is formed in the same manner as the perfluoropolyether oil emulsion.

EXAMPLES

The following describes the present invention with reference to Examples.

Reference Example 1

(1) In a 1-L capacity, four-necked flask equipped with a thermometer and a receiver for removing low-boiling substances, 500 g (0.78 mol) of a compound of the formula: $CF_3(CF_2)_3(CH_2CF_2)(CF_2CF_2)_2(CH_2CH_2)I$ (990 C %), and 181 g (1.56 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 91 g (0.78 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 412 g (yield: 78%) of a purified reaction product (96 GC %).

The results of $^1$H-NMR and $^{19}$F-NMR confirmed that the resulting purified reaction product was a compound represented by the following formula:

$CF_3(CF_2)_3(CH_2CF_2)(CF_2CF_2)_2(CH_2CH_2)P(O)(OCH_2CH_3)_2$ (2) In a 1-L capacity, four-necked flask equipped with a thermometer and a condenser, 300 g (0.44 mol) of the polyfluoroalkylphosphonic acid diester of the formula: $CF_3(CF_2)_3(CH_2CF_2)(CF_2CF_2)_2(CH_2CH_2)P(O)(OCH_2CH_3)_2$ (96GC %) obtained in step (1) above, and 300 g of about 35% concentrated hydrochloric acid were charged, and the mixture was stirred at 100° C. for 12 hours. After cooling, filtration under reduced pressure was performed to thereby collect 276 g of solid matters. The solid matters were washed with water and filtrated again, further followed by acetone washing and filtration, thereby obtaining 242 g (0.41 mol; yield: 92%) of the target product.

The results of $^1$H-NMR and $^{19}$F-NMR confirmed that the resulting reaction product was the target compound (polyfluoroalkylphosphonic acid) represented by the following formula:

$CF_3(CF_2)_3(CH_2CF_2)(CF_2CF_2)_2(CH_2CH_2)P(O)(OH)_2$ (IIa)

Reference Example 2

(1) In a 1-L, four-necked flask equipped with a thermometer and a receiver for removing low-boiling substances, 500 g (0.92 mol) of a compound of the formula:

$CF_3(CF_2)_3(CH_2CF_2)(CF_2CF_2)(CH_2CH_2)I(99\ GC\ \%)$ and 213 g (1.84 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 107 g (0.92 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 142° C. The distillate fraction was washed with water, thereby obtaining 407 g (yield: 79%) of a purified reaction product (98 GC %).

The results of $^1$H-NMR and $^{19}$F-NMR confirmed that the resulting purified reaction product was a compound represented by the following formula:

$CF_3(CF_2)_3(CH_2CF_2)(CF_2CF_2)(CH_2CH_2)P(O)(OCH_2CH_3)_2$ (2) In a 1-L, four-necked flask equipped with a thermometer and a condenser, 300 g (0.53 mol) of the obtained polyfluoroalkylphosphonic acid diester of the formula:

$CF_3(CF_2)_3(CH_2CF_2)(CF_2CF_2)(CH_2CH_2)P(O)(OCH_2CH_3)_2(96\ GC\ \%)$ and 300 g of about 35% concentrated hydrochloric acid were charged, and the mixture was stirred at 100° C. for 12 hours. After cooling, filtration under reduced pressure was performed to thereby collect 287 g of solid matters. The solid matters were washed with water and filtrated again, further followed by acetone washing and filtration, thereby obtaining 240 g (0.49 mol; yield: 93%) of the target product.

The results of $^1$H-NMR and $^{19}$F-NMR confirmed that the resulting product was the target compound (polyfluoroalkylphosphonic acid) represented by the following formula:

$CF_3(CF_2)_3(CH_2CF_2)(CF_2CF_2)(CH_2CH_2)P(O)(OH)_2$ (IIb)

Reference Example 3

(1) In a 1-L capacity, four-necked flask equipped with a thermometer and a receiver for removing low-boiling substances, 500 g (0.76 mol) of a compound of the formula: $CF_3(CF_2)(CH_2CF_2)(CF_2CF_2)_3(CH_2CH_2)I$ (97 GC %), and 176 g (1.52 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 88 g (0.76 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 395 g (yield: 77%) of a purified reaction product (96 GC %).

The results of $^1$H-NMR and $^{19}$F-NMR confirmed that the resulting purified reaction product was a compound represented by the following formula:

$$CF_3(CF_2)(CH_2CF_2)(CF_2CF_2)_3(CH_2CH_2)P(O)(OCH_2CH_3)_2$$

(2) In a 1-L capacity, four-necked flask equipped with a thermometer and a condenser, 300 g (0.44 mol) of the polyfluoroalkylphosphonic acid diester of the formula: $CF_3(CF_2)(CH_2CF_2)(CF_2CF_2)_3(CH_2CH_2)P(O)(OCH_2CH_3)_2$ (96 GC %) obtained in step (1) above, and 300 g of about 35% concentrated hydrochloric acid were charged, and the mixture was stirred at 100° C. for 12 hours. After cooling, filtration under reduced pressure was performed to thereby collect 276 g of solid matters. The solid matters were washed with water and filtrated again, further followed by acetone washing and filtration, thereby obtaining 237 g (0.40 mol; yield: 90%) of the target product.

The results of $^1$H-NMR and $^{19}$F-NMR confirmed that the resulting reaction product was the target compound (polyfluoroalkylphosphonic acid) represented by the following formula:

$$CF_3(CF_2)(CH_2CF_2)(CF_2CF_2)_3(CH_2CH_2)P(O)(OH)_2 \quad (IIc)$$

Reference Example 4

(1) In a 1-L, four-necked flask equipped with a thermometer and a receiver for removing low-boiling substances, 500 g (0.90 mol) of a compound of the formula:

$$CF_3(CF_2)(CH_2CF_2)(CF_2CF_2)_2(CH_2CH_2)I (97\ GC\ \%)$$

and 208 g (1.80 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 104 g (0.90 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 142° C. The distillate fraction was washed with water, thereby obtaining 397 g (yield: 78%) of a purified reaction product (97 GC %).

The results of $^1$H-NMR and $^{19}$F-NMR confirmed that the resulting purified reaction product was a compound represented by the following formula:

$$CF_3(CF_2)(CH_2CF_2)(CF_2CF_2)_2(CH_2CH_2)P(O)(OCH_2CH_3)_2$$

(2) In a 1-L, four-necked flask equipped with a thermometer and a condenser, 300 g (0.52 mol) of the obtained polyfluoroalkylphosphonic acid diester of the formula:

$$CF_3(CF_2)(CH_2CF_2)(CF_2CF_2)_2(CH_2CH_2)P(O)(OCH_2CH_3)_2 (95\ GC\ \%)$$

and 300 g of about 35% concentrated hydrochloric acid were charged, and the mixture was stirred at 100° C. for 12 hours. After cooling, filtration under reduced pressure was performed to thereby collect 271 g of solid matters. The solid matters were washed with water and filtrated again, further followed by acetone washing and filtration, thereby obtaining 235 g (0.48 mol; yield: 92%) of the target product.

The results of $^1$H-NMR and $^{19}$F-NMR confirmed that the resulting product was the target compound (polyfluoroalkylphosphonic acid) represented by the following formula:

$$CF_3(CF_2)(CH_2CF_2)(CF_2CF_2)_2(CH_2CH_2)P(O)(OH)_2 \quad (IId)$$

Reference Example 5

(1) In a 1-L capacity, four-necked flask equipped with a thermometer and a receiver for removing low-boiling substances, 500 g (0.88 mol) of a compound of the formula: $CF_3(CF_2)(CH_2CF_2)(CF_2CF_2)_2(CH_2CH_2)_2I$ (97 GC %), and 204 g (1.76 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 104 g (0.90 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 140 to 142° C. The distillate fraction was washed with water, thereby obtaining 410 g (yield: 79%) of a purified reaction product (97 GC %).

The results of $^1$H-NMR and $^{19}$F-NMR confirmed that the resulting purified reaction product was a compound represented by the following formula:

$$CF_3(CF_2)(CH_2CF_2)(CF_2CF_2)_2(CH_2CH_2)_2P(O)(OCH_2CH_3)_2$$

(2) In a 1-L capacity, four-necked flask equipped with a thermometer and a condenser, 300 g (0.51 mol) of the polyfluoroalkylphosphonic acid diester of the formula: $CF_3(CF_2)(CH_2CF_2)(CF_2CF_2)_2(CH_2CH_2)_2P(O)(OCH_2CH_3)_2$ (97 GC %) obtained in step (1) above, and 300 g of about 35% concentrated hydrochloric acid were charged, and the mixture was stirred at 100° C. for 12 hours. After cooling, filtration under reduced pressure was performed to thereby collect 269 g of solid matters. The solid matters were washed with water and filtrated again, further followed by acetone washing and filtration, thereby obtaining 240 g (0.46 mol; yield: 90%) of the target product.

The results of $^1$H-NMR and $^{19}$F-NMR confirmed that the resulting reaction product was the target compound (polyfluoroalkylphosphonic acid) represented by the following formula:

$$CF_3(CF_2)(CH_2CF_2)(CF_2CF_2)_2(CH_2CH_2)_2P(O)(OH)_2 \quad (IIe)$$

Reference Example 6

(1) In a 1-L, four-necked flask equipped with a thermometer and a receiver for removing low-boiling substances, 500 g (1.12 mol) of a compound of the formula:

$$CF_3(CF_2)(CH_2CF_2)(CF_2CF_2)(CH_2CH_2)I (98\ GC\ \%)$$

and 259 g (2.24 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 130 g (1.12 mol) per batch, and the mixture was stirred for 18 hours in total.

After the reaction was completed, the reaction mixture was subjected to simple distillation under reduced pressure at an internal pressure of 0.2 kPa, an internal temperature of 130 to 140° C., and an overhead temperature of 128 to 131° C. The distillate fraction was washed with water, thereby obtaining 405 g (yield: 79%) of a purified reaction product (98 GC %).

The results of $^1$H-NMR and $^{19}$F-NMR confirmed that the resulting purified reaction product was a compound represented by the following formula:

$$CF_3(CF_2)(CH_2CF_2)(CF_2CF_2)(CH_2CH_2)P(O)(OCH_2CH_3)_2$$

(2) In a 1-L, four-necked flask equipped with a thermometer and a condenser, 300 g (0.63 mol) of the obtained polyfluoroalkylphosphonic acid diester of the formula:

$$CF_3(CF_2)(CH_2CF_2)(CF_2CF_2)(CH_2CH_2)P(O)(OCH_2CH_3)_2 \quad (94\text{ GC \%})$$

and 300 g of about 35% concentrated hydrochloric acid were charged, and the mixture was stirred at 100° C. for 12 hours. After cooling, filtration under reduced pressure was performed to thereby collect 262 g of solid matters. The solid matters were washed with water and filtrated again, further followed by acetone washing and filtration, thereby obtaining 229 g (0.59 mol; yield: 93%) of the target product.

The results of $^1$H-NMR and $^{19}$F-NMR confirmed that the resulting product was the target compound (polyfluoroalkylphosphonic acid) represented by the following formula:

$$CF_3(CF_2)(CH_2CF_2)(CF_2CF_2)(CH_2CH_2)P(O)(OH)_2 \quad \text{(IIf)}$$

Example 1

In a 200-ml reactor equipped with a stirrer and a dropping funnel, 53.2 g of water heated to 40° C. was charged while keeping the water warm, and 5 g (8.4 mmol) of the polyfluoroalkylphosphonic acid [IIa] obtained in Reference Example 1 was added thereto. Then, 15.4 g (12.7 mmol) of an aqueous ammonia solution with a concentration of 1.4 wt. % was added, and stirring was continued for one hour to perform neutralization. As a result, an aqueous solution of polyfluoroalkylphosphonic acid ammonium salt having a pH of 8 (active ingredient concentration: 7.0 wt. %) was obtained [emulsifier aqueous solution I].

The emulsifier aqueous solution I was gradually added to water, and the surface tension of the aqueous solution was measured. The critical micelle concentration [CMC] of the solution was 0.8 wt. %, and the surface tension at a concentration of 2.0 wt. % was 17 mN/m. The surface tension was measured at 20° C. by the maximum bubble method using a dynamic surface tensiometer (produced by SITA).

Comparative Example 1

In Example 1, when stirring was carried out for one hour without adding an aqueous ammonia solution to the polyfluoroalkylphosphonic acid [IIa], the added polyfluoroalkylphosphonic acid [IIa] was not dissolved in water and was separated. As a result, no aqueous solution was obtained.

Examples 2 to 6

In Example 1, the amounts of water and aqueous ammonia solution of a concentration of 1.4 wt. % were changed to predetermined amounts, and the same amount (5 g) of each of the polyfluoroalkylphosphonic acids [IIb] to [IIf] respectively obtained in Reference Examples 2 to 6 was used in place of the polyfluoroalkylphosphonic acid [IIa]. Consequently, their aqueous solutions (active ingredient concentration: 7.0 wt. %) were obtained [emulsifier aqueous solutions II to VI].

The surface tension (CMC and surface tension at a concentration of 2.0 wt. %) of the emulsifier aqueous solutions II to VI was measured in the same manner. Table 1 below shows the obtained results, together with the composition of the emulsifier aqueous solutions. The results of Example 1 are also shown.

TABLE 1

|  | Ex. 1 | Ex. 2 | Ex. 3 | Ex. 4 | Ex. 5 | Ex. 6 |
|---|---|---|---|---|---|---|
| [Emulsifier aqueous solution] | | | | | | |
| Symbol | I | II | III | IV | V | VI |
| Phosphonic acid | | | | | | |
| Symbol | IIa | IIb | IIc | IId | IIe | IIf |
| g number | 5 | 5 | 5 | 5 | 5 | 5 |
| mmol number | 8.4 | 10.2 | 8.4 | 10.2 | 9.6 | 17.1 |
| Aqueous ammonia solution | | | | | | |
| g number | 15.4 | 18.5 | 15.4 | 13.8 | 15.7 | 23.2 |
| mmol number | 12.7 | 15.2 | 12.7 | 15.2 | 14.4 | 25.7 |
| Water | | | | | | |
| g number | 53.2 | 50.5 | 53.2 | 55.2 | 53.3 | 47.6 |
| [Surface tension] | | | | | | |
| CMC (wt. %) | 0.8 | 0.8 | 0.8 | 1.0 | 0.9 | 1.2 |
| Surface tension at 2% concentration (mN/m) | 17.0 | 16.8 | 16.9 | 18.2 | 18.5 | 19.0 |

Reference Example 7

In Example 1, the amount of water was changed to 66.4 g, and 5 g (11.6 mmol) of pentadecafluorooctanoic acid ammonium salt $C_7F_{15}COONH_4$ (EFTOP EF204 produced by Jemco Co., Ltd.) was used in place of the polyfluoroalkylphosphonic acid [IIa] and aqueous ammonia solution, thereby preparing an aqueous solution thereof (active ingredient concentration: 7.0 wt. %) [emulsifier aqueous solution VII].

When the surface tension of the emulsifier aqueous solution VII was measured in the same manner, the CMC of the solution was 0.8 wt. %, and the surface tension at a concentration of 2 wt. % was 18 mN/m.

Example 7

In a 1,000-ml reactor equipped with a stirrer and a dropping funnel, 186 g of water heated to 40° C. was charged while keeping the water warm, and 214 g of the emulsifier aqueous solution I and 100 g of perfluoropolyether oil represented by the general formula:

$$C_3F_7O[CF(CF_3)CF_2O]_mC_2F_5 \quad (m: 2\text{ to }100)$$

(BARRIERTA J 25 FLUID, produced by NOK Kluber Co., Ltd.; kinetic viscosity (40° C.): 25 mm$^2$/s) were added thereto (the total amount of the mixture: 500 g). Subsequently, preliminary emulsification was carried out for two minutes using a homogenizer at a rotational speed of 3,000 rpm. Emulsification was further carried out using a high-pressure homogenizer (produced by Nippon Seiki Co., Ltd.) at a pressure of 600 kgf/cm$^2$ (58.8 MPa), thereby obtaining 485 g (recovery rate: 97%) of perfluoropolyether oil emulsion A (the amount of polyfluoroalkylphosphonic acid ammonium salt was 15.0 parts by weight based on 100 parts by weight of perfluoropolyether oil).

The average particle diameter of the obtained perfluoropolyether oil emulsion A was 150 nm. The emulsion A was allowed to stand for one month at room temperature and 40° C., and the average particle diameters then measured were 152 nm and 157 nm, respectively. It was thus confirmed that the formed emulsion was stable in both cases. The average particle diameter was measured by a dynamic light-scattering method using a particle size distribution analyzer (Microtrac UPA150, produced by Nikkiso Co., Ltd.).

Comparative Example 2

In Example 7, the amount of water was changed to 385 g, and 15 g of polyfluoroalkylphosphonic acid [IIa] was used in place of the emulsifier aqueous solution I. As a result, the mixture immediately underwent liquid-liquid separation, and no emulsion was formed.

Reference Example 8

In Example 7, the same amount (214 g) of emulsifier aqueous solution VII was used in place of the emulsifier aqueous solution I, thereby obtaining 482 g (recovery rate: 96%) of perfluoropolyether oil emulsion J. The average particle diameter of the emulsion J was 131 nm, the average particle diameter after one month at room temperature was 136 nm, and the average particle diameter after one month at 40° C. was 140 nm. It was thus confirmed that the formed emulsion was stable.

Examples 8 to 15

In Example 7, the same amount (214 g) of emulsifier aqueous solution I or each of the emulsifier aqueous solutions II to VI in place of the emulsifier aqueous solution I was used, and the same amount (100 g) of perfluoropolyether oil J25, J100, or J400 represented by the same general formula or perfluorodecalin $C_{10}F_{18}$ was used, thereby obtaining perfluoropolyether oil emulsions B to I.

Perfluoropolyether oil J25: as described above
Perfluoropolyether oil J100: BARRIERTA J100 FLUID, produced by NOK
Kluber Co., Ltd.; kinetic viscosity (40° C.): 95 mm$^2$/s
Perfluoropolyether oil J400: BARRIERTA J400 FLUID, produced by NOK
Kluber Co., Ltd.; kinetic viscosity (40° C.):
390 mm$^2$/s As for these emulsions, the initial average particle diameter ($d_0$), the average particle diameter after one month at room temperature ($d_1$), and the average particle diameter after one month at 40° C. ($d_2$) were measured. Further, the rates of increase in particle size ($d_1-d_0$)/$d_0\times100$(%) and ($d_2-d_0$)/$d_0\times100$(%) were calculated. Table 2 below shows the obtained results, together with the properties of the emulsions. The measurement results of Example 7 are also shown.

TABLE 2

| | | Example | | | | | | | | |
|---|---|---|---|---|---|---|---|---|---|---|
| | | 7 | 8 | 9 | 10 | 11 | 12 | 13 | 14 | 15 |
| Emulsion | | | | | | | | | | |
| Symbol | | A | B | C | D | E | F | G | H | I |
| Emulsifier aqueous solution | | | | | | | | | | |
| Symbol | | I | I | I | I | II | III | IV | V | VI |
| Polyether oil | | | | | | | | | | |
| J25 | (g) | 100 | — | — | — | — | — | — | — | — |
| J100 | (g) | — | 100 | — | — | 100 | 100 | 100 | 100 | 100 |
| J400 | (g) | — | — | 100 | — | — | — | — | — | — |
| $C_{10}F_{18}$ | (g) | — | — | — | 100 | — | — | — | — | — |
| Recovery amount | (g) | 485 | 480 | 481 | 476 | 483 | 478 | 480 | 486 | 475 |
| Recovery rate | (%) | 97 | 96 | 96 | 95 | 97 | 96 | 96 | 97 | 95 |
| Average particle size | | | | | | | | | | |
| Initial ($d_0$) | (nm) | 150 | 147 | 142 | 145 | 145 | 140 | 160 | 155 | 172 |
| After one month at room temperature ($d_1$) | (nm) | 152 | 150 | 145 | 143 | 148 | 142 | 165 | 160 | 175 |
| After one month at 40° C. ($d_2$) | (nm) | 157 | 152 | 145 | 146 | 147 | 148 | 170 | 165 | 176 |
| Particle size increase rate | | | | | | | | | | |
| ($d_1 - d_0$)/$d_0 \times 100$ | (%) | +1 | +2 | +2 | −1 | +2 | +1 | +3 | +3 | +2 |
| ($d_2 - d_0$)/$d_0 \times 100$ | (%) | +5 | +3 | +2 | +1 | +1 | +6 | +6 | +7 | +2 |

Example 16

The perfluoropolyether oil emulsion A (2 parts by weight) was added, while stirring, to 98 parts by weight of ion exchange water for dilution, thereby preparing a mold-releasing agent emulsion.

Using the mold-releasing agent emulsion, mold release test in urethane rubber molding was performed as follows. An aluminum cup (45 mm in diameter and 50 mm in depth) was used as a mold. After the mold was heated to 80° C., the mold-releasing agent was applied thereto and dried at 80° C. Into the mold, to which the mold-releasing agent had been applied, 10 g of a mixture of 100 parts by weight of urethane prepolymer (Coronate 4090, produced by Nippon Polyurethane Industry Co., Ltd.) heated to 80° C. and 12.8 parts by weight of a methylenebis(o-chloroaniline) curing agent (Iharacuamine MT, produced by Ihara Chemical Industry Co., Ltd.) heated to 120° C. was poured, and cured by heating at 120° C. for one hour.

Before curing, a hook was stood in the center of the mold for removing the cured molded product. When the load required to pull the hook to take out the molded product from the mold after curing was measured by a spring scales positioned above the mold, the result was 9 N (mold releasability). Further, when how many times a one-time application of the mold-releasing agent allowed mold releasing at a mold release load of 50 N or less was measured, the result was 5 times (mold release life).

Examples 17 to 26

In Example 16, the kind and amount (part by weight) of perfluoropolyether oil emulsion used in the preparation of mold-releasing agent emulsions, and the kind (water: ion exchange water, EtOH: ethanol, IPA: isopropanol) and used amount (part by weight) of diluent were each changed as shown in the following table. Table 3 below shows the measurement results of mold releasability and mold release life, together with the measurement results of Example 16.

TABLE 3

| Example | Emulsion Kind | Emulsion Amount | Diluent Water | Diluent EtOH | Diluent IPA | Mold releasability (N) | Mold release life (time) |
|---|---|---|---|---|---|---|---|
| Ex. 16 | A | 2 | 98 | — | — | 9 | 5 |
| Ex. 17 | B | 2 | 98 | — | — | 9 | 5 |
| Ex. 18 | B | 0.5 | 99.5 | — | — | 12 | 4 |
| Ex. 19 | C | 2 | 98 | — | — | 10 | 5 |
| Ex. 20 | D | 2 | 98 | — | — | 12 | 5 |
| Ex. 21 | E | 2 | 98 | — | — | 13 | 4 |
| Ex. 22 | F | 2 | 98 | — | — | 15 | 3 |
| Ex. 23 | G | 2 | 98 | — | — | 16 | 2 |
| Ex. 24 | H | 2 | 98 | — | — | 16 | 2 |
| Ex. 25 | B | 2 | 83 | 15 | — | 9 | 5 |
| Ex. 26 | B | 2 | 83 | — | 15 | 8 | 6 |

Comparative Example 3

In Example 16, the mold releasability and mold release life were measured without applying a mold-releasing agent emulsion. The results were not measurable because the molded product was not removed from the mold, and consequently the mold release life was 0 times.

The invention claimed is:

1. An emulsifier comprising, as an active ingredient, a polyfluoroalkylphosphonic acid salt represented by the general formula:

$$C_nF_{2n+1}(CH_2CF_2)_a(CF_2CF_2)_b(CH_2CH_2)_cP(O)(OM^1)(OM^2) \quad [I]$$

wherein $M^1$ is a hydrogen atom, an alkali metal, an ammonium base, or an organic amine base, $M^2$ is an alkali metal, an ammonium base, or an organic amine base, n is an integer of 1 to 6, a is an integer of 1 to 4, b is an integer of 1 to 3, and c is an integer of 1 to 3.

2. The emulsifier according to claim 1, which is prepared as an aqueous solution of an organic solvent solution.

3. An emulsion comprising the emulsifier according to claim 2, and a perfluoropolyether oil or a perfluorocarbon compound.

4. The emulsion according to claim 3, wherein the perfluoropolyether oil is represented by the general formula:

$$RfO(C_3F_6O)_p(C_2F_4O)_q(CF_2O)_nRf' \quad [XI]$$

wherein Rf and Rf' are perfluoro-lower alkyl groups having 1 to 5 carbon atoms, $C_3F_6$, $C_2F_4O$, and $CF_2O$ groups are bonded randomly, p+q+r is an integer of 2 to 200, and p, q, or r may be 0, or the general formula:

$$F(CF_2CF_2CF_2O)_nC F_2CF_3 \quad [XII]$$

wherein n is an integer of 2 to 100.

5. The emulsion according to claim 4, wherein the perfluoropolyether oil [X] is a perfluoropolyether oil [Xia] represented by the general formula:

$$RfO[CF(CF_3)CF_2O]_mRf'$$

wherein Rf and Rf' are perfluoro-lower alkyl groups having 1 to 5 carbon atoms, and m is an integer of 2 to 200.

6. A mold-releasing agent comprising the emulsifier according to claim 1 as an active ingredient.

7. The mold-releasing agent of claim 6, wherein the polyfluoroalkylphosphonic acid is used as an ammonium salt.

8. The mold-releasing agent according to claim 6, which is prepared as an aqueous solution or organic solvent solution of the polyfluoroalkylphosphonic acid salt.

9. An emulsion-type mold-releasing agent comprising the polyfluoroalkylphosphonic acid salt solution according to claim 8 and a perfluoropolyether oil.

10. The emulsion-type mold-releasing agent according to claim 9, wherein the perfluoropolyether oil is a perfluoropolyether oil represented by the general formula:

$$RfO(C_3F_6O)_p(C_2F_4O)_q(CF_2O)_nRf' \quad [XI]$$

wherein Rf and Rf' are perfluoro-lower alkyl groups having 1 to 5 carbon atoms, $C_3F_6$, $C_2F_4O$, and $CF_2O$ groups are bonded randomly, p+q+r is an integer of 2 to 200, and p, q, or r may be 0, or the general formula:

$$F(CF_2CF_2CF_2O)_nC F_2C F_3 \quad [XII]$$

wherein n is an integer of 2 to 100.

11. The emulsion-type mold-releasing agent according to claim 10, wherein a perfluoropolyether oil [Xia] represented by the general formula:

$$RfO[CF(CF_3)CF_2O]_mRf'$$

wherein Rf and Rf' are perfluoro-lower alkyl groups having 1 to 5 carbon atoms, and m is an integer of 2 to 200, is used.

12. A mold-releasing agent comprising an aqueous solution or organic solution in which the emulsion-type mold-releasing agent according to claim 9 is further diluted with an aqueous medium or an organic solvent so as to have a solid matters content of 0.01 to 30 wt. %.

13. The mold-releasing agent according to claim 12, which is applied to a molding mold for use.

14. A surface-treating agent comprising an aqueous solution or organic solvent solution in which the perfluoropolyether oil emulsion according to claim 3 is further diluted with an aqueous medium or an organic solvent.

15. The surface-treating agent according to claim 14, which is used as a water- and oil-repellent agent or an anti-adhesion agent.

16. An oxygen transport medium or a storage solution for isolated organs, comprising the perfluorocarbon compound emulsion according to claim 3.

* * * * *